United States Patent
Kaethner et al.

(10) Patent No.: US 11,918,309 B2
(45) Date of Patent: Mar. 5, 2024

(54) IMAGING A ROBOTICALLY MOVED MEDICAL OBJECT

(71) Applicant: Siemens Healthcare GmbH, Erlangen (DE)

(72) Inventors: Christian Kaethner, Forchheim (DE); Andreas Meyer, Bubenreuth (DE); Michael Wiets, Langensendelbach (DE)

(73) Assignee: Siemens Healthcare GmbH, Erlangen (DE)

( * ) Notice: Subject to any disclaimer, the term of this patent is extended or adjusted under 35 U.S.C. 154(b) by 486 days.

(21) Appl. No.: 17/212,179

(22) Filed: Mar. 25, 2021

(65) Prior Publication Data

US 2021/0315649 A1 Oct. 14, 2021

(30) Foreign Application Priority Data

Apr. 9, 2020 (DE) .......................... 102020204574.7

(51) Int. Cl.
*A61B 34/32* (2016.01)
*A61B 6/12* (2006.01)
(Continued)

(52) U.S. Cl.
CPC ............... *A61B 34/32* (2016.02); *A61B 6/12* (2013.01); *A61B 34/20* (2016.02);
(Continued)

(58) Field of Classification Search
CPC ... A61B 34/20; A61B 34/32; A61B 2034/303; A61B 6/12; A61B 2090/376; A61M 25/0113
See application file for complete search history.

(56) References Cited

U.S. PATENT DOCUMENTS 7,974,681 B2   7/2011   Wallace et al.
9,237,930 B2   1/2016   Hauck
(Continued)

FOREIGN PATENT DOCUMENTS

CN   101524279 A    9/2009
EP     2931127 B1    2/2018
WO   2006124148 A2   11/2006

OTHER PUBLICATIONS

German Office Action for German Application No. 10 2020 204 574.7 dated Jan. 29, 2021.

*Primary Examiner* — Chao Sheng
(74) *Attorney, Agent, or Firm* — Lempia Summerfield Katz LLC

(57) ABSTRACT

A system for imaging a robotically moved medical object has a movement device for robotic movement of the medical object, a medical imaging device, and a processing unit. The processing unit is configured to receive a data set that maps a vessel structure of an examination object and is registered with the medical imaging device, and to determine an object path along the vessel structure toward a target region in the data set. The movement device is configured to move the medical object along the object path and provide an object parameter relating to a movement state of the medical object. The processing unit is further configured to control a positioning of the medical imaging device relative to the examination object as a function of object parameter and object path such that a predefined section of the medical object is mapped in image data acquired by the medical imaging device.

17 Claims, 3 Drawing Sheets

(51) Int. Cl.
    *A61B 34/20*     (2016.01)
    *A61B 34/30*     (2016.01)
    *A61B 90/00*     (2016.01)
    *A61M 25/01*     (2006.01)

(52) U.S. Cl.
    CPC ... *A61B 2034/303* (2016.02); *A61B 2090/376* (2016.02); *A61M 25/0113* (2013.01)

(56) References Cited

U.S. PATENT DOCUMENTS

| | | |
|---|---|---|
| 2005/0256398 A1 | 11/2005 | Hastings et al. |
| 2006/0258935 A1 | 11/2006 | Pile-spellman et al. |
| 2007/0025508 A1 | 2/2007 | Ohishi |
| 2008/0281181 A1 | 11/2008 | Manzione et al. |
| 2009/0082784 A1 | 3/2009 | Meissner et al. |
| 2009/0137952 A1 | 5/2009 | Ramamurthy et al. |
| 2009/0192385 A1 | 7/2009 | Meissner et al. |
| 2011/0230758 A1 | 9/2011 | Eichler |
| 2012/0215094 A1 | 8/2012 | Rahimian et al. |
| 2012/0238871 A1 | 9/2012 | Pfister |
| 2014/0309658 A1 | 10/2014 | Murphy et al. |
| 2015/0342556 A1* | 12/2015 | Van Dijk ............... A61B 6/547 600/434 |
| 2019/0231436 A1 | 8/2019 | Panse et al. |

* cited by examiner

IMAGING A ROBOTICALLY MOVED MEDICAL OBJECT

The present patent document claims the benefit of German Patent Application No. 10 2020 204 574.7, filed Apr. 9, 2020, which is hereby incorporated by reference in its entirety.

TECHNICAL FIELD

Interventional medical procedures in or via a vessel system of an examination object may require, in particular percutaneous, introduction of a medical object into the vessel system. Furthermore, for a successful diagnosis and/or treatment, it may be necessary to guide at least part of the medical object toward a target region in the vessel system that is to be treated.

BACKGROUND

For this, the medical object may be moved, in particular manually, by a medical operator with regular radiographic monitoring. One disadvantage of this is the high exposure of the medical operator and the examination object to X-ray radiation.

Furthermore, tracking of the X-ray apparatus may be necessary for radiographic monitoring in order to check a location of the medical object in the vessel system. The X-ray apparatus may be tracked, for example, based on image information of the most recently acquired X-ray image in each case and/or based on a positioning signal from a positioning system for localization of the medical object in the vessel system. Drawbacks in this case, however, are the fault susceptibility when tracking the X-ray apparatus and the increased operating effort for the medical operator.

SUMMARY AND DESCRIPTION

The object underlying the disclosure is therefore to enable precise and intuitive imaging-based checking of a movable medical object. The scope of the present disclosure is defined solely by the appended claims and is not affected to any degree by the statements within this summary. The present embodiments may obviate one or more of the drawbacks or limitations in the related art.

In a first aspect, a system is provided for imaging a robotically moved medical object. The system has a movement device for robotic movement of the medical object, a medical imaging device, and a processing unit. Furthermore, the processing unit is configured to receive a data set. The data set at least partially maps a vessel structure of an examination object and is registered with the medical imaging device. In addition, the processing unit is configured to determine an object path along the vessel structure toward a target region in the data set. Furthermore, the movement device is configured to move the medical object along the object path and to provide an object parameter relating to a movement state of the medical object. The processing unit is also configured to control a positioning of the medical imaging device relative to the examination object as a function of the object parameter and the object path in such a way that a predefined section of the medical object is mapped in image data acquired by the medical imaging device.

The medical object may be a surgical instrument and/or diagnostic instrument. In particular, the medical object may be elongated and/or flexible. For example, the medical object may be a catheter and/or endoscope and/or guide wire.

The medical imaging device may be a medical X-ray apparatus, (e.g., a medical C-arm X-ray apparatus), a computed tomography system (CT), a sonography system, a magnetic resonance system (MRT), a positron emission tomography system (PET), or a combination thereof. Advantageously, the medical imaging device may be moved relative to the examination object and/or relative to the movement device. Furthermore, the medical imaging device may be configured to map at least one detail of the examination object, in particular of the vessel structure. For this, the medical imaging device may be configured to acquire, for example, two-dimensionally and/or three-dimensionally spatially resolved image data from the examination object. The image data may also be temporally resolved. The medical imaging device may further be configured to map at least part of the medical object, (e.g., the predefined section and/or a marker structure), in the image data.

Advantageously, the movement device may be a robotic device, which is configured for remote manipulation of the medical object, for example, a catheter robot. Advantageously, the movement device may have a fastening element, in particular a movable and/or displaceable one. Furthermore, the movement device may have a cassette element, which is configured for the acquisition of at least part of the medical object. Furthermore, the movement device may have a movement element, which is fastened to the fastening element, for example, a stand and/or robotic arm. In addition, the fastening element may be configured to fasten the movement element to a patient supporting device. Furthermore, the movement element may advantageously have at least one actuator element, (e.g., an electric motor), with the processing unit being configured for controlling the actuator element. Advantageously, the cassette element may be coupled, (e.g., mechanically and/or electromagnetically and/or pneumatically), to the movement element, in particular the at least one actuator element. The cassette element may also have at least one transmission element, which may be moved by way of the coupling between the cassette element and the movement element, in particular the at least one actuator element. For example, the at least one transmission element may be movement-coupled to the at least one actuator element. Advantageously, the transmission element is configured to transmit a movement of the actuator element to the medical object in such a way that the medical object is moved along a longitudinal extension direction of the medical object and/or that the medical object is rotated around the longitudinal extension direction. The at least one transmission element may have a pulley, roller, slit, or a combination thereof.

Advantageously, the movement element may have a plurality of, in particular independently controllable, actuator elements. Furthermore, the cassette element may have a plurality of transmission elements, in particular at least one movement-coupled transmission element, for each of the actuator elements. This may enable, in particular independent and/or simultaneous, movement of the medical object along different degrees of freedom of movement.

Advantageously, the movement device is arranged outside of the examination object. Furthermore, the movement device may be configured to control and/or move at least one section of the medical object arranged in the examination object. For example, the movement device may be configured to deform a tip of the medical object in a defined manner, for example, by way of a cable inside the medical object.

Advantageously, the processing unit may have at least one input element, (e.g., a keyboard, a joystick, a pedal, a capacitive input field, or a combination thereof), which enables control of the movement device by a user, (e.g., a medical operator), by way of a corresponding operator input. This may enable control of the movement of the medical object in the examination object by the movement device by way of a user input at the input element.

The processing unit is advantageously configured to receive a data set, which at least partially maps the vessel structure of the examination object. The examination object may be a human or animal patient and/or a phantom, in particular a vessel phantom. Advantageously, the vessel structure may have a spatial arrangement, in particular a vascular tree, of at least one vessel section, (e.g., a blood vessel and/or a hollow organ), of the examination object.

Receiving the data set may include capturing and/or reading from a computer-readable data memory and/or receiving from a data memory unit, for example, a database. Furthermore, the data set may be provided by a provision unit of a further medical imaging device. The further medical imaging device may be the same as or different from the medical imaging device. The further medical imaging device may a medical X-ray apparatus, (e.g., a medical C-arm X-ray apparatus), a computed tomography system (CT), a sonography system, a magnetic resonance system (MRT), a positron emission tomography system (PET), or a combination thereof.

The data set may have, (e.g., two-dimensional and/or three-dimensional and/or four-dimensional), first image data from the examination object, (e.g., of the vessel structure), which may be acquired preoperatively. Furthermore, the data set may have a model, in particular a three-dimensional one, (e.g., a volume network model and/or a central line model), of the vessel structure. The model may be determined based on the first image data. The data set may have a segmented mapping of the vessel structure of the examination object.

Furthermore, the data set, (e.g., the mapping of the vessel structure), is registered with the medical imaging device. In other words, a coordinate system of the data set may advantageously be registered with the coordinate system of the medical imaging device. A corresponding spatial position in the coordinate system of the medical imaging device may be assigned to each position in the data set hereby. In addition, the data set may advantageously be registered with a positioning, (e.g., an instantaneous one), of the examination object. Advantageously, the examination object may be arranged on a patient supporting device, wherein the fastening element of the movement device may be fastened to the patient supporting device, in particular stationarily in respect of the patient supporting device. Advantageously, the positioning of the examination object may describe a spatial position and/or orientation and/or location of the examination object.

Advantageously, the processing unit may have a presentation unit, (e.g., a screen and/or monitor and/or a capacitive and/or resistive display), which is configured to the display of information from the movement device and/or the data set and/or further information. Furthermore, the processing unit, in particular the input element, may be configured to enable determining of a target region in the data set. In particular, the target region in the data set may be determined by way of a user input by the input element. In particular, the user may identify the target region based on a display of the data set by the presentation unit and determine it by the input element. The target region may describe a position and/or a region in or on the vessel structure in the data set. In particular, the target region may be determined in the data set based on image information, for example, an intensity value and/or contrast value and/or an annotation and/or an anatomical characteristic, in particular an anatomical landmark.

Advantageously, the processing unit may also be configured to determine an initial region based on information relating to an entry point of the medical object into the examination object. Advantageously, the initial region may mark a position in the data set, in particular on the vessel structure, at which the medical object enters into the vessel structure of the examination object. The processing unit may be configured to register the positioning of the examination object with the data set based on the position at which the medical object enters into the vessel structure of the examination object. The entry point of the medical object into the examination object may be arranged, in particular, on an introducer sheath for the medical object.

The processing unit may be configured to determine the initial region based on a user input by the input element and/or based on further image data. Furthermore, the processing unit may be configured to determine the object path along the vessel structure in such a way that the medical object may be moved, starting from the initial region toward the target region. For this, the processing unit may be configured to apply a path planning algorithm to the data set. Advantageously, the processing unit may be configured to take into account at least one material property of the medical object, for example, a diameter and/or an elasticity and/or a deformability on determination of the object path. The object path may be two-dimensional and/or three-dimensional. Furthermore, the object path may include information relating to vessel branchings, in particular bifurcations, and/or vessel curvatures and/or vessel anomalies, (e.g., aneurysms), in route to the target region.

Furthermore, the processing unit, (e.g., the presentation unit), may be configured for graphic display of the object path. In particular, the object path may be displayed in an overlaid representation with the data set.

The movement device may be configured to move the medical object, in particular part of the medical object, which is arranged in the examination object, along the object path. The movement device may be configured to move the medical object along the longitudinal extension direction of the medical object and/or around the longitudinal extension direction in such a way that the part of the medical object, which is arranged inside the examination object, (e.g., the vessel structure), follows the object path. In addition, the movement device may be configured to deform and/or orient the tip of the medical object in a defined manner, (e.g., by a rotational movement), in such a way that this tip follows the object path. This may be helpful in the case of vessel branchings, for example, a bifurcation and/or an orifice.

Advantageously, the movement device is configured to provide an object parameter relating to a movement state of the medical object. The object parameter may include information relating to a relative movement of the medical object in respect of the movement device. Advantageously, the object parameter may include information relating to the, (e.g., instantaneous), movement state of the medical object relative to the movement device.

The processing unit may also be configured to determine a position of a predefined section of the medical object, (e.g., the tip of the medical object), in the vessel structure, (e.g., the data set), based on the object parameter and the object path. Because the data set is registered with the medical imaging device, the processing unit may also be configured to determine a spatial position of the predefined section of the medical object in the coordinate system of the medical imaging device. The predefined section of the medical object may be the tip of the medical object and/or a section having a marker structure.

Advantageously, the processing unit is configured to control the positioning of the medical imaging device relative to the examination object in such a way that the predefined section of the medical object is mapped in image data acquired by the medical imaging device. The positioning of the medical imaging device relative to the examination object may describe a spatial relative positioning. In particular, the spatial relative positioning may describe an orientation and/or spatial position of the medical imaging device in respect of the examination object and vice versa. In particular, the examination object and the medical imaging device may be moved relative to each other. Advantageously, the processing unit may be configured for coordinated positioning of the medical imaging device relative to the examination object based on the determined position of the predefined section of the medical object in the coordinate system of the medical imaging device. In particular, the processing unit may be configured to control the positioning of the medical imaging device relative to the examination object in such a way that the predefined section of the medical object is mapped in a predefined image point, in particular an image center, and/or field of view of the image data acquired by the medical imaging device and/or is arranged in an isocenter of the medical imaging device.

Furthermore, the medical imaging device may have an imaging direction, (e.g., a projection direction), along which imaging direction the image data is acquired from the examination object. Advantageously, the processing unit may be configured to control the positioning of the medical imaging device relative to the examination object in such a way that the predefined section of the medical object runs substantially perpendicular to the imaging direction. Advantageously, the positioning may be controlled in such a way that the predefined section of the medical object is located in a mapping plane of the medical imaging device, which runs, in particular, perpendicular to the imaging direction. This may enable the predefined section in the image data acquired by the medical imaging device to be captured particularly well.

In a further advantageous embodiment of the proposed system, the movement device may be configured to provide the object parameter including information relating to a speed and/or an orientation and/or relative position and/or movement distance of the medical object.

The movement device may have a sensor unit configured for detection of a movement of the medical object relative to the movement device. The sensor unit may have an encoder, (e.g., a wheel encoder and/or a roller encoder), and/or an optical sensor, (e.g., a barcode scanner and/or a laser scanner and/or a camera), and/or an electromagnetic sensor. For example, the sensor unit may be arranged so as to be at least partially integrated in the movement element, in particular the at least one actuator element, and/or the cassette element, in particular the at least one transmission element. Alternatively, or in addition, the movement device may be configured to provide the object parameter based on a control parameter for controlling the at least one actuator element and/or the at least one transmission element. Furthermore, the sensor unit may be configured for providing the object parameter to the processing unit. The sensor unit may be configured for detection of the relative movement of the medical object by detection of the medical object relative to the movement device. Alternatively, or in addition, the sensor unit may be configured for detection of a movement and/or change in location of components of the movement device, which components are movement-coupled to the medical object, for example, the at least one actuator element and/or the at least one transmission element.

The object parameter may have information relating to a speed, (e.g., a movement speed), of the medical object relative to the movement device. The information relating to the speed of the medical object may include information relating to a translational speed of the medical object along the longitudinal extension direction thereof and/or information relating to a rotational speed of the medical object about the longitudinal extension direction thereof.

Furthermore, the object parameter may include information relating to the orientation and/or relative position and/or movement distance of the medical object. Advantageously, the movement device, (e.g., the sensor unit), may be configured to determine the, in particular instantaneous, relative position and/or orientation and/or movement distance in respect of a reference positioning of the medical object at a reference instant, in particular an earlier instant. Advantageously, the movement device, (e.g., the sensor unit), may be configured for detecting the reference positioning of the medical object when a predefined section of the medical object is arranged in the initial region, in particular the entry point and/or the introducer sheath. In particular, the reference positioning may include information relating to the spatial position and/or orientation of the medical object, in particular of the predefined section. For example, the movement device, (e.g., the sensor unit), may be configured to detect a movement state of the medical object on the movement device and/or a state of the movement device, in particular of components of the movement device movement-coupled to the medical object, at the reference instant.

Furthermore, the movement device may be configured for detecting a change in the movement state of the medical object in respect of the reference positioning. Based on the detected change in the movement state of the medical object, the movement device may be configured to provide the object parameter to the processing unit. For example, the processing unit may be configured to determine a movement distance of the medical object, (e.g. in the vessel structure of the examination object), between the reference positioning and the, in particular instantaneous, positioning of the medical object based on the detected change in the state of the medical object on the movement device. The movement distance may describe a spatial distance between the reference positioning and the instantaneous positioning of the medical object along the longitudinal extension direction thereof. In particular, the longitudinal extension direction of the medical object may run in a spatially curved manner. Because, from the entry point, the medical object is arranged along the object path in the vessel structure, the processing unit may be configured for determining the relative and/or absolute spatial positioning of the medical object, in particular of the predefined section.

Advantageously, this may enable accurate determination of the, in particular relative and absolute, spatial positioning of the medical object, in particular of the predefined section, in the vessel structure of the examination object without additional imaging.

Furthermore, the processing unit may be configured to control the positioning of the medical imaging device relative to the examination object based on the determined spatial positioning of the medical object, in particular of the predefined section, in such a way that the predefined section is mapped in image data acquired by the medical imaging device. The positioning of the medical imaging device relative to the examination object may be controlled based on the object parameter, which object parameter is provided by the movement device, and the object path, therefore.

In a further advantageous embodiment of the proposed system, the processing unit may be configured to repeatedly determine the positioning of the medical imaging device upon a change in the object parameter and/or the object path.

A change in the object parameter may describe a change in the movement state of the medical object. Advantageously, the processing unit may be configured, following a change in the movement state of the medical object, to determine a changed spatial positioning of the predefined section of the medical object in the vessel structure, (e.g., along the object path), based on the, (e.g., most recently determined), object parameter. Furthermore, the processing unit may be configured for repeated determination of the positioning of the medical imaging device relative to the examination object based on the changed spatial positioning of the predefined section of the medical object.

Furthermore, a change in the object path may occur due to a changed, in particular movement-induced, positioning of the examination object and/or a change in the target region, for example, by way of a user input by the input element. In particular, an actual object path may be specified as the object path. The actual object path may be determined by medical imaging and/or a positioning system for spatial ordering of the medical object and/or an input by the user by the input element. In particular, the actual object path may exhibit a deviation with respect to the object path. Advantageously, the actual object path describes the actual arrangement of the medical object in the vessel structure of the examination object.

This may enable particularly precise and, at the same time, flexible control of the positioning of the medical imaging device relative to the examination object.

In a further advantageous embodiment of the proposed system, the processing unit may be configured to determine the positioning of the medical imaging device as a function of a threshold value in respect of the change in the object parameter and/or the object path.

The threshold value may describe a minimum change in the object parameter and/or the object path, with the processing unit being configured for, in particular repeated, determination of the positioning of the medical imaging device relative to the examination object when the threshold value is exceeded. For example, the threshold value may be specified in respect of the change in the object parameter and/or the object path based on an acquisition parameter of the medical imaging device and/or based on a user input by the input element. In particular, the threshold value may be specified as a function of a geometric dimension of a field of view (FOV) of the medical imaging device. Advantageously, the threshold value may be specified in such a way that the positioning of the medical imaging device is repeatedly determined by the processing unit if the predefined section of the medical object is no longer mapped in the image data acquired and/or to be acquired by the medical imaging device. Advantageously, unnecessary movement of the medical imaging device and/or the examination object for repositioning on changes in the object parameter and/or the object path below the threshold value may be avoided hereby.

Furthermore, a change in the object path may then also make repeated determining of the positioning of the medical imaging device relative to the examination object necessary if the predefined section is mapped in the image data acquired by the medical imaging device. For example, an orientation of the predefined section of the medical object may run substantially parallel to an imaging direction of the medical imaging device due to the changed object path. The processing unit may be configured to determine the positioning of the medical imaging device based on the changed object path and the object parameter in such a way that the predefined section of the medical object runs substantially perpendicular to the imaging direction of the medical imaging device.

Alternatively, or in addition, the threshold value may describe a maximum change in the object parameter and/or the object path, wherein the processing unit may be configured to determine the spatial positioning of the predefined section of the medical object based on additional information when the threshold value is exceeded. The additional information may be provided by a positioning system for spatial positioning of the medical object and/or by a user input by the input element and/or by the medical imaging device.

Advantageously, this may provide the exact localization of the predefined section of the medical object in the vessel structure along the object path within a confidence region of the system.

In a further advantageous embodiment of the proposed system, the system may furthermore include a patient supporting device, which is configured for supporting the examination object. The processing unit may be configured to control a movement of the patient supporting device and/or the medical imaging device in such a way that the medical imaging device is positioned relative to the examination object and a predefined section of the medical object is mapped in image data acquired by the medical imaging device.

The patient supporting device may be configured as a patient table and/or examination table. Furthermore, the patient supporting device may be at least partially movable. Furthermore, the patient supporting device may advantageously be configured to move at least part of the examination object, in particular relative to the medical imaging device. Furthermore, the processing unit may be configured for controlling the patient supporting device, in particular to control a movement of at least part of the patient supporting device. Advantageously, the patient supporting device may be configured to provide positioning information for, in particular instantaneous, spatial positioning of the examination object arranged on the patient supporting device to the processing unit. Advantageously, a coordinate system of the examination object may be registered with the coordinate system of the patient supporting device and the coordinate system of the medical imaging device. The patient supporting device may be configured to be at least partially rotatable and/or tiltable and/or pivotable and/or displaceable. If the movement device is fastened, in particular stationarily, to the patient supporting device, the movement device may also be moved, in particular stationarily in respect of the examination object, when the patient supporting device is moved.

The processing unit may be configured to control the movement of the patient supporting device, in particular of the examination object arranged thereon, in such a way that the predefined section of the medical object, which is arranged along the object path in the vessel structure of the medical object, is mapped in image data acquired by the medical imaging device. This may be advantageous when the medical imaging device is at least partially immobile, in particular is stationary, in respect of the examination object.

Alternatively, or in addition, the medical imaging device may be movable at least partially in respect of the examination object and/or in respect of the patient supporting device. Advantageously, a spatial position and/or an orientation of the medical imaging device in respect of the examination object may be controlled by the processing unit hereby. The medical imaging device may be configured to be at least partially rotatable and/or tiltable and/or pivotable and/or displaceable. This may be advantageous, in particular, when the patient supporting device is at least partially immobile, in particular stationary, in respect of the medical imaging device.

Advantageously, the processing unit may be configured for controlling the medical imaging device, in particular for controlling a movement of the medical imaging device. If the patient supporting device and the medical imaging device are each at least partially movable, the processing unit may be configured for coordinated control of the patient supporting device and the medical imaging device. This may enable particularly flexible and, at the same time, precise positioning of the medical imaging device relative to the examination object, which is arranged on the patient supporting device, by way of control of the processing unit.

In a further advantageous embodiment of the proposed system, the processing unit may be configured to adjust the object path based on the object parameter upon a deformation of the vessel structure due to the medical object arranged therein.

The introduction of the medical object into the vessel structure may cause a deformation of at least one vessel section around the medical object to occur, in particular when the medical object has a greater rigidity than the vessel section. Upon a deformation of the at least one vessel section, a deformation, corresponding therewith, of the object path may also occur. This may lead to a discrepancy between the spatial positioning of the predefined section of the medical object to be determined by the processing unit and an actual spatial positioning of the predefined section. Advantageously, the processing unit may be configured to adjust, in particular to deform, the object path based on the, in particular instantaneous, object parameter. Furthermore, the processing unit may be configured to adjust, in particular to deform, the data set analogously to the object path. For this, the object parameter may, in particular additionally, include a material parameter and/or operating parameter of the medical object. Furthermore, the data set may include, in particular spatially resolved, information relating to a deformability, in particular elasticity of the vessel structure.

This may enable particularly precise control of the medical imaging device and/or patient supporting device for mapping the predefined section of the medical object in the image data.

In a further advantageous embodiment of the proposed system, the medical imaging device may be a medical X-ray apparatus, in particular, a medical C-arm X-ray apparatus. The processing unit may also be configured to additionally control the positioning of the medical imaging device relative to the examination object in such a way that an X-ray dose is optimized, in particular minimized, for acquisition of the image data.

The positioning of the medical imaging device may describe a spatial position and angulation in respect of the examination object. Furthermore, the medical imaging device may be configured to illuminate a region of the examination object for mapping by X-ray beams and to detect this after interaction with the examination object. Absorption of at least some of the X-ray beams may occur during the interaction of the X-ray beams with the examination object. Depending on the spatial dimension and, in particular material, composition of the examination object, the absorbed part of the X-ray beams may vary. In the case of an examination object with a spatially inhomogeneous construction, depending on angulation, a different X-ray dose may be necessary in order to map the predefined section of the medical object in the image data acquired and/or to be acquired by the medical imaging device. Advantageously, the processing unit may be configured to control the positioning, in particular the angulation, of the medical imaging device in such a way that the predefined section of the medical object is mapped in the image data and, at the same time, the X-ray dose is optimized, in particular minimized, for acquisition of the image data.

The X-ray dose for acquisition of the image data may be optimized, in particular minimized, while maintaining the feasibility for the predefined section of the medical object to be mapped in the image data.

In a further advantageous embodiment of the proposed system, the processing unit may be configured for receiving at least one positioning suggestion based on the object parameter and the object path. Furthermore, the processing unit may be configured for determining the positioning of the medical imaging device based on the at least one positioning suggestion.

The at least one positioning suggestion may be specified based on at least one anatomical and/or geometric feature along the object path in the vessel structure. In particular, the data set may include information relating to the at least one positioning suggestion. Furthermore, the at least one positioning suggestion may be specified by a user input by the input element. The at least one positioning suggestion may include a standard angulation of the medical imaging device relative to at least one section of the object path, based on the at least one anatomical feature. Advantageously, the at least one positioning suggestion may be specified as a function of the, in particular instantaneous, positioning of the predefined section of the medical object along the object path as a boundary condition and/or explicitly to the processing unit for control of the positioning of the medical imaging device. The processing unit may be configured for determining the, in particular instantaneous, positioning of the predefined section of the medical object along the object path based on the object parameter and the object path.

In particular, the processing unit may be configured for receiving a plurality of positioning suggestions based on the object parameter and the object path. Based on the object parameter, the object path and the plurality of positioning suggestions, the processing unit may also be configured to determine an optimum positioning, in particular with respect to an X-ray dose and/or feasibility for the predefined section to be mapped in the image data, in particular to select from the plurality of positioning suggestions. In addition, the processing unit may be configured to control the medical imaging device and/or the patient supporting device into the determined, in particular selected, positioning.

The positioning of the medical imaging device relative to the examination object may additionally be determined based on at least one anatomical and/or geometric feature of the vessel structure along the object path.

In a second aspect, a method is provided for control of a medical imaging device. In act a), a data set is received, wherein the data set at least partially maps a vessel structure of an examination object. Furthermore, the data set is registered with the medical imaging device. In act b), a target region is determined in the data set. In act c), an object path along the vessel structure toward the target region is determined in the data set. In act i1), an object parameter relating to a movement state of a medical object is received, wherein the medical object is arranged along the object path. In act i2), a spatial position of a predefined section of the medical object is determined based on the parameter and the object path. Hereafter in act i3), a positioning of the medical imaging device relative to the examination object is determined based on the spatial position in such a way that the predefined section of the medical object may be mapped by the medical imaging device. In act i4), the medical imaging device is moved into the determined positioning. In act i5), image data is acquired from the examination object by the medical imaging device.

The advantages of the proposed method for control of a medical imaging device substantially correspond to the advantages of the proposed system. Features, advantages, or alternative embodiments mentioned in this connection may likewise be transferred to the other claimed subject matters and vice versa.

Receiving the data set and/or the object parameter may include capturing and/or reading from a computer-readable data memory and/or receiving from a data memory unit, for example, a database. The data set may be provided by a provision unit of a further medical imaging device. Furthermore, the object parameter may be provided by a movement device for remote manipulation of a medical object and/or by a user input by an input element.

In particular, the target region in the data set may be determined by a user input by the input element. In particular, the user may identify the target region based on a display of the data set by the presentation unit and determine it by the input element. The target region may describe a position and/or a region in or on the vessel structure in the data set. In particular, the target region may be determined in the data set based on image information, for example, an intensity value and/or contrast value and/or an annotation and/or an anatomical characteristic, in particular an anatomical landmark.

The object path may be determined in act c) along the vessel structure toward the target region in the data set, in particular, by applying an algorithm for path planning to the data set. Furthermore, the object path may be at least partially determined and/or adjusted by a user input by the input element.

The object parameter may include information relating to an orientation and/or relative position and/or movement distance of the medical object, in particular the predefined section, in respect of a reference point, in particular in respect of the movement device. Because the data set is registered with the medical imaging device, advantageously, a position in a coordinate system of the medical imaging device may be assigned to each position in a coordinate system of the data set. The spatial position of the predefined section may be determined in act i2), in particular in the coordinate system of the medical imaging device, based on the object path and the object parameter, which may describe the position of the predefined section of the medical object in the data set.

Advantageously, the object path may have a two-dimensional and/or three-dimensional spatial course, in particular along a central line of at least one vessel section of the vessel structure. In addition, the object path may have an additionally temporally-resolved four-dimensional course. Furthermore, at any position the object path may have a running direction along which the medical object, in particular the predefined section, is arranged. Information relating to the spatial orientation of the predefined section of the medical object may also be determined based on the spatial position determined in act i2) and the object path. Advantageously, in act i3), the positioning of the medical imaging device relative to the examination object may be determined based on the spatial position and the object path in such a way that the predefined section of the medical object may be mapped by the medical imaging device. The positioning of the medical imaging device relative to the examination object may be determined in such a way that the predefined section may be mapped in a predefined image point and/or field of view and/or in a predefined orientation in image data to be acquired by the medical imaging device.

The medical imaging device may be at least partially movable in respect of the examination object. In act i4), the medical imaging device may be moved into the positioning determined in act i3). Hereafter, the image data may be acquired from the examination object by the medical imaging device. Advantageously, the image data may have two-dimensional and/or three-dimensional mapping of at least one detail of the examination region, in particular the vessel structure, and of the medical object arranged along the object path. Advantageously, the predefined section of the medical object is mapped in the image data.

In a further advantageous embodiment of the proposed method, acts i1) to i5) may be repeatedly performed upon a change in the object parameter and/or the object path. In particular, upon a change in the object parameter and/or the object path, a comparison may be made with a specified threshold value, with acts i1) to i5) only being repeatedly performed when the specified threshold value is exceeded. An unnecessary movement of the medical imaging device on a slight change in the object parameter and/or object path may be avoided hereby. Advantageously, the threshold value may be specified in such a way that acts i1) to i5) are only repeatedly performed if the predefined section of the medical object cannot be mapped in the image data.

In a further advantageous embodiment of the proposed method, the object parameter may include information relating to a movement distance of the medical object in respect of a spatial reference point. When a distance threshold is exceeded the object parameter may be calibrated based on the image data and the determined positioning of the medical imaging device.

The spatial reference point may mark, for example, a spatial position on the movement device and/or on the examination object, in particular along the object path. In particular, the spatial reference point may identify a starting point of the object path, with the target region identifying an end point of the object path.

The movement distance may describe a spatial distance between the spatial reference point and the, in particular instantaneous, spatial position of the predefined section along the object path, running, in particular, in a curved manner. Because the vessel structure may have different diameters along the object path, a meandering of the medical object may occur inside at least one vessel section. If the data set includes three-dimensionally resolved information relating to course and dimensions, in particular diameter, of the vessel structure, a differing arrangement of the medical object at a distance from the object path, which runs, for example, along a central line, may be taken into account on calibration of the object parameter. In particular, an actual movement distance of the predefined section along the object path may be compared with the movement distance of the medical object that has meandered and be used for calibration.

Furthermore, the, in particular most recently acquired, image data may be used to determine the actual movement distance of the predefined section along the object path. The spatial position of the predefined section in respect of the vessel section of the vessel structure mapped in the image data may be determined based on the image data. Because the positioning of the medical imaging device at the instant of acquisition of the image data is known and the medical imaging device is registered with the data set, the actual spatial position of the predefined section may be determined. Hereafter, the actual movement distance of the predefined section may be determined in respect of the spatial reference point along the object path. Advantageously, the actual movement distance may be specified as the movement distance for calibration of the object parameter.

Alternatively or in addition, a correction factor may be determined based on a comparison of the movement distance with the actual movement distance. Upon a change in the object parameter, this change may be scaled with the correction factor. Advantageously, a deviation between the actual movement distance and the movement distance may be reduced hereby.

In a third aspect, a medical imaging device is provided, which is configured for carrying out a proposed method for control of a medical imaging device.

The medical imaging device may be a medical X-ray apparatus, e.g., a medical C-arm X-ray apparatus, a computed tomography system (CT), a sonography system, a magnetic resonance system (MRT), a positron emission tomography system (PET), or a combination thereof. Advantageously, the medical imaging device may be moved relative to the examination object and/or relative to the movement device and/or relative to the patient supporting device. Furthermore, the medical imaging device may be configured to map at least one detail of the examination object, in particular the vessel structure. For this, the medical imaging device may be configured to acquire, in particular two-dimensional and/or three-dimensional, image data from the examination object. The medical imaging device may also be configured to map at least part of the medical object, in particular the predefined section and/or a marker structure, in the image data.

The medical imaging device may also be configured for receiving the data set and/or for providing the image data. Providing image data may include storing on a computer-readable storage medium and/or transmitting to the processing unit.

Furthermore, the proposed system, in particular the processing unit, may be configured for carrying out a proposed method for control of a medical imaging device.

The advantages of the proposed medical imaging device substantially correspond to the advantages of the proposed system. Features, advantages, or alternative embodiments mentioned in this connection may likewise be transferred to the other claimed subject matters and vice versa.

In a fourth aspect, a computer program product is provided, which includes a program and may be loaded directly into a memory of a programmable arithmetic unit and has program modules or components, (e.g., libraries and help functions), in order to carry out a method for control of a medical imaging device when the computer program product is executed. The computer program product may include software with a source code, which still has to be compiled and linked or which just has to be interpreted, or an executable software code, which just has to be loaded into the processing unit for execution. As a result of the computer program product, the method for control of a medical imaging device may be carried out quickly, in a manner that may be repeated identically and robustly. The computer program product is configured such that it may perform the method acts by the processing unit. The processing unit has in each case to exhibit the prerequisites such as, for example, an appropriate main memory, an appropriate graphics card or an appropriate logic unit, so the respective method acts may be performed efficiently.

The computer program product is stored, for example, on a computer-readable medium or stored on a network or server from where it may be loaded into the processor of a processing unit, which may be directly connected to the processing unit or be configured as part of the processing unit. Furthermore, control information of the computer program product may be stored on an electronically readable data carrier. The control information of the electronically readable data carrier may be configured in such a way that it carries out a method when the data carrier is used in a processing unit. Examples of electronically readable data carriers are a DVD, a magnetic tape, or a USB stick on which electronically readable control information, in particular software, is stored. When this control information is read from the data carrier and stored in a processing unit, all embodiments of the above-described methods may be carried out. The disclosure may thus also start from the computer-readable medium and/or the electronically readable data carrier. The advantages of the proposed computer program product substantially correspond to the advantages of the proposed method.

BRIEF DESCRIPTION OF THE DRAWINGS

Exemplary embodiments of the disclosure are illustrated in the drawings and will be described in more detail hereinafter. Identical reference numerals will be used in different figures for identical features. In the drawings.

DETAILED DESCRIPTION

Figure 1:
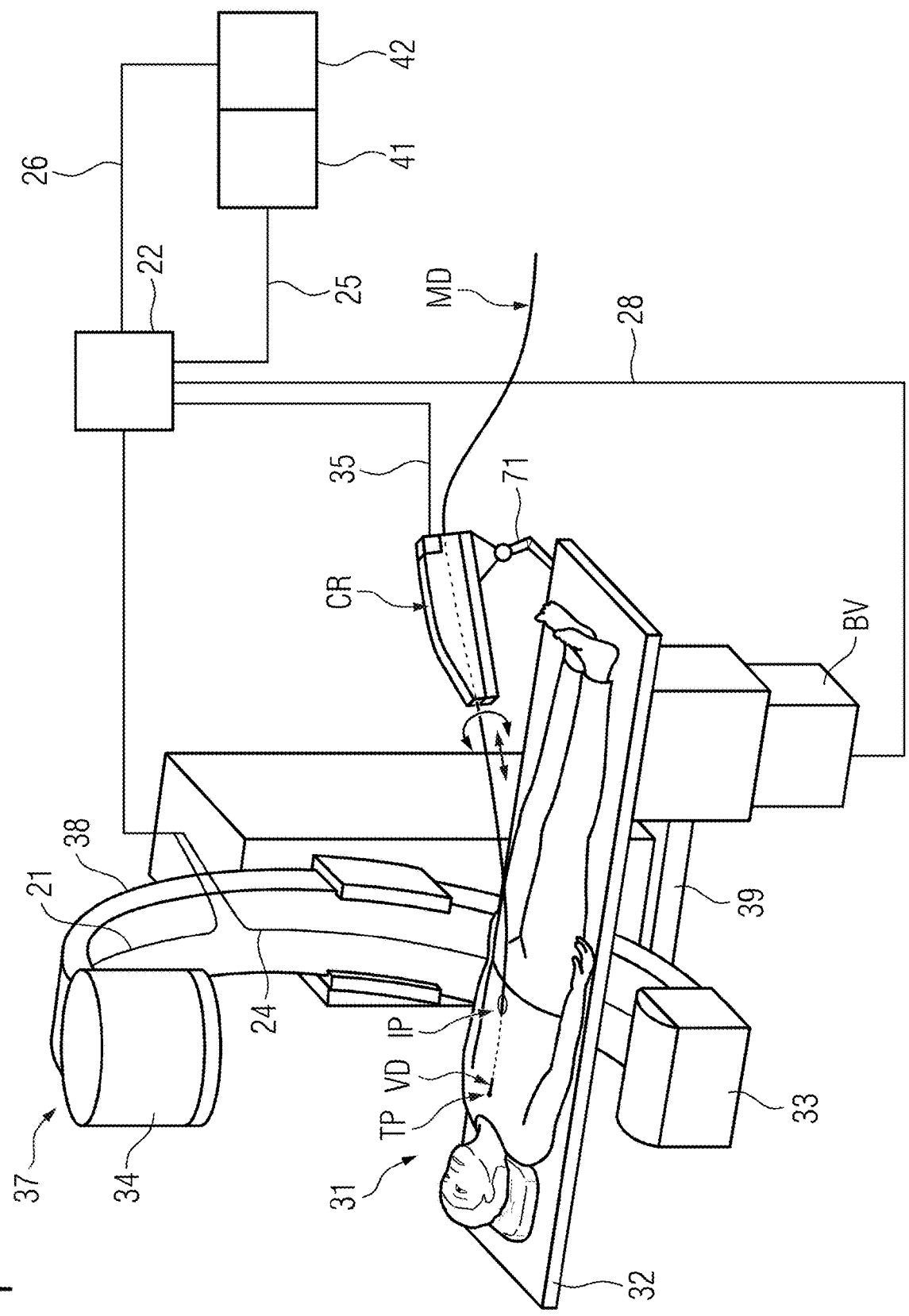
FIG. 1 depicts a schematic representation of an embodiment of the proposed system for imaging a robotically moved medical object.

FIG. 1 depicts a schematic representation of an advantageous embodiment of the proposed system for imaging a robotically moved medical object MD. The system may have a movement device CR for robotic movement of the medical object MD, a medical imaging device, and a processing unit 22. A medical C-arm X-ray apparatus 37 is shown by way of example of a proposed medical imaging device. The processing unit 22 may be configured to receive a data set, which at least partially maps a vessel structure of an examination object 31 and is registered with the medical imaging device. Advantageously, the examination object 31 may be arranged on and/or at a patient supporting device 32.

Furthermore, the processing unit 22 may be configured to determine an object path along the vessel structure toward a target region in the data set. The movement device CR may be configured, for example, as a catheter robot, in particular for remote manipulation of the medical object MD. Furthermore, the movement device CR may be configured for movement of the medical object MD along the object path. The movement device CR may also be configured for providing an object parameter relating to a movement state of the medical object MD to the processing unit 22.

Advantageously, the medical object MD may be introduced into the examination object 31, in particular the vessel structure, by an introducer sheath at an entry point IP. Furthermore, the movement device CR may be fastened, in particular movably, by a fastening element 71, (e.g., a stand and/or robotic arm), to the patient supporting device 32. Advantageously, the movement device CR may be configured to move the medical object MD arranged therein in a translational manner at least along a longitudinal extension direction of the medical object. Furthermore, the movement device CR may be configured to rotate the medical object MD around the longitudinal extension direction. Alternatively or in addition, the movement device may be configured for controlling a movement of at least part of the medical object MD, in particular at a distal end of the medical object MD. For example, the at least one part of the medical object MD may be curved.

The processing unit 22 may also be configured to control a positioning of the medical imaging device 37 relative to the examination object 31 as a function of the object parameter and the object path in such a way that a predefined section VD of the medical object MD is mapped in image data acquired by the medical imaging device 37. The predefined section VD may describe, for example, a tip and/or a section having a marker structure on the medical object MD. The medical object MD may be configured as a surgical instrument, in particular an elongate one, and/or diagnostic instrument. In particular, the medical object MD may be flexible and/or mechanically deformable. The medical object MD may be configured as a catheter and/or endoscope and/or guide wire.

The medical imaging device in the exemplary embodiment as a medical C-arm X-ray apparatus 37 may have a detector unit 34 and an X-ray source 33. For acquisition of the image data, the arm 38 of the medical C-arm X-ray apparatus 37 may be mounted so as to move around one or a plurality of axes. Furthermore, the medical C-arm X-ray apparatus 37 may include a movement device 39, which enables a movement of the medical C-arm X-ray apparatus 37 in the space.

For acquisition of the image data of the examination object 31 arranged on the patient supporting device 32, the processing unit 22 may send a signal 24 to the X-ray source 33. The X-ray source 33 may then emit an X-ray beam bundle, in particular a cone beam and/or fan beam and/or parallel beam. When the X-ray beam bundle, after an interaction with the examination region of the examination object 31 to be mapped, strikes a surface of the detector unit 34, the detector unit 34 may send a signal 21 to the processing unit 22. The processing unit 22 may receive the image data, for example, with the aid of the signal 21.

Furthermore, the processing unit may include an input element 42, (e.g., a keyboard and/or pointing device, in particular a computer mouse), and/or a presentation unit 41, (e.g., a monitor and/or display). The input element 42 may be integrated in the presentation unit 41, for example, in the case of a capacitive and/or resistive input display. Control, in particular supplementary control, of the medical C-arm X-ray apparatus 37 and/or the movement device CR and/or the patient supporting device 32 may be enabled by a user input at the input element 42. For this, the input element 42 may send, for example, a signal 26 to the processing unit 22.

Furthermore, the presentation unit 41 may be configured to display information and/or graphic representations of information from the medical C-arm X-ray apparatus 37 and/or the processing unit 22 and/or the movement device CR, (e.g., the object parameter), and/or further components. For this, the processing unit 22 may send, for example, a signal 25 to the presentation unit 41. In particular, the presentation unit 41 may be configured to display a graphic representation of the data set and/or the image data.

In the illustrated exemplary embodiment, the processing unit 22 may also be configured to additionally control the positioning of the medical imaging device in the embodiment as a medical (C-arm) X-ray apparatus 37 in such a way that an X-ray dose is optimized, in particular minimized, for acquisition of the image data.

The processing unit 22 may also be configured for receiving at least one positioning suggestion based on the object parameter and the object path. The processing unit 22 may be configured for determining the positioning of the medical C-arm X-ray apparatus 37 relative to the examination object 31 based on the at least one positioning suggestion.

The at least one positioning suggestion may be specified, for example, based on at least one anatomical and/or geometric feature along the object path in the vessel structure. In particular, the data set may include information relating to the at least one positioning suggestion. Furthermore, the at least one positioning suggestion may be specified by a user input by the input element 41. The at least one positioning suggestion may have a standard angulation, based on at least one anatomical feature, of the medical imaging device relative to at least one section of the object path, for example, a right-hand coronary artery. Advantageously, the positioning of the medical C-arm X-ray apparatus 37 may be determined differently from the at least one positioning suggestion by the processing unit 22 if the section of the vessel structure along the object path exhibits a difference, for example, an anatomical variation.

Furthermore, the processing unit 22 may be configured for controlling the movement device CR. For this, the processing unit 22 may send a corresponding signal 35 to the movement device CR. In addition, the movement device CR may provide the object parameter by the, in particular bidirectional, signal 35 to the processing unit 22.

Furthermore, the patient supporting device 32 may be at least partially movable. For this, the patient supporting device 32 may advantageously have a movement device BV, which movement device BV may be controlled by a signal 28 from the processing unit 22.

The processing unit 22 may be configured to control a movement of the patient supporting device 32 and/or the medical C-arm X-ray apparatus 37 in such a way that the medical C-arm X-ray apparatus 37 is positioned relative to the examination object 31 and at the same time the predefined section VD of the medical object is mapped in image data acquired by the medical C-arm X-ray apparatus 37.

Figure 2:
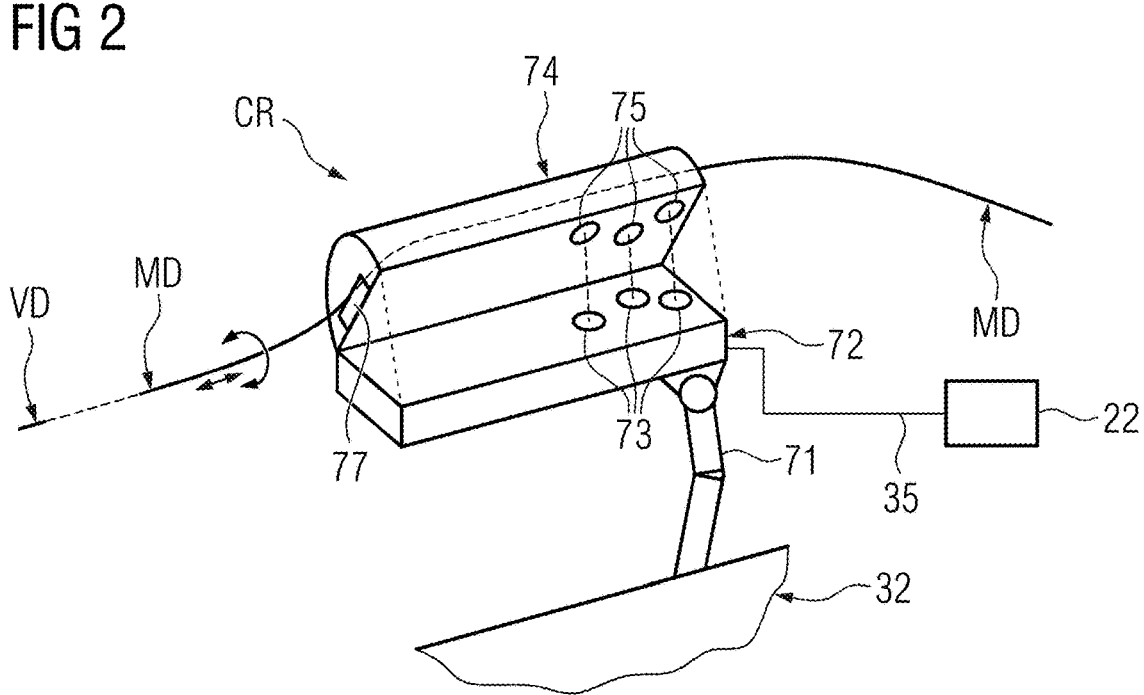
FIG. 2 depicts a schematic representation of an example of a movement device for robotic movement of a medical object.

FIG. 2 depicts a schematic representation of a movement device CR for robotic movement of a medical object MD. Advantageously, the movement device CR may have a fastening element 71, in particular a moveable and/or displaceable one. Furthermore, the movement device CR may have a cassette element 74 configured for acquisition of at least part of the medical object MD. Furthermore, the movement device CR may have a movement element 72 fastened to the fastening element 71, for example, a stand and/or robotic arm. In addition, the fastening element 71 may be configured to fasten the movement element 72 to the patient supporting device 32, in particular movably. Furthermore, the movement element 72 may advantageously have at least one, (e.g., three), actuator element(s) 73, for example, an electric motor, wherein the processing unit 22 is configured for controlling the at least one actuator element 73. Advantageously, the cassette element 74 may be coupled, (e.g., mechanically and/or electromagnetically and/or pneumatically), to the movement element 72, in particular the at least one actuator element 73. The cassette element 74 may also have at least one transmission element 75, which may be moved by the coupling between the cassette element 74 and the movement element 72, in particular the at least one actuator element 73. In particular, the at least one transmission element 75 may be movement-coupled to the at least one actuator element 73. Furthermore, the transmission element 75 may be configured to transmit a movement of the actuator element 73 to the medical object MD in such a way that the medical object MD is moved along a longitudinal extension direction of the medical object MD and/or that the medical object MD is rotated around the longitudinal extension direction. The at least one transmission element 75 may have a pulley and/or roller and/or slit.

Advantageously, the movement element 72 may have a plurality of, in particular independently controllable, actuator elements 73. Furthermore, the cassette element 74 may have a plurality of transmission elements 75, in particular at least one movement-coupled transmission element 75 for each of the actuator elements 73. This may enable, (e.g., independent and/or simultaneous), movement of the medical object MD along different degrees of freedom of movement.

Furthermore, the movement device CR, in particular the at least one actuator element 73, may be controlled by the signal 35 from the processing unit 22. The movement of the medical object MD may be controlled, in particular indirectly, by the processing unit 22 hereby. In addition, an orientation and/or a position of the movement device CR relative to the examination object 31 may be adjusted by a movement of the fastening element 71. Advantageously, the movement device CR is configured for providing the object parameter to the processing unit 22.

For this, the movement device CR may have a sensor unit 77 configured for detection of a movement of the medical object MD relative to the movement device CR. The sensor unit 77 may have an encoder, (e.g., a wheel encoder and/or a roller encoder), an optical sensor, (e.g., a barcode scanner and/or a laser scanner and/or a camera), an electromagnetic sensor, or a combination thereof. For example, the sensor unit 77 may be arranged so as to be at least partially integrated in the movement element 72, (e.g., the at least one actuator element 73), and/or the cassette element 74, (e.g., the at least one transmission element 75). Alternatively or in addition, the movement device CR may be configured to provide the object parameter based on a control parameter for controlling the at least one actuator element 73 and/or the at least one transmission element 74. Furthermore, the sensor unit 77 may be configured for providing the object parameter to the processing unit 22. The sensor unit may be configured for detection of the relative movement of the medical object MD by way of a detection of the medical object MD relative to the movement device. Alternatively or in addition, the sensor unit 77 may be configured for detection of a movement and/or change in location of components of the movement device CR, which components are movement-coupled to the medical object MD, for example, the at least one actuator element 73 and/or the at least one transmission element 74.

The movement device CR may be configured to provide the object parameter including information relating to a speed and/or an orientation and/or a relative position and/or movement distance of the medical object MD. Furthermore, the processing unit 22 may be configured to repeatedly determine the positioning of the medical imaging device upon a change in the object parameter and/or the object path OP, in particular as a function of a threshold value in respect of the change in the object parameter and/or the object path OP.

A change in the object parameter and/or the object path may describe a change in the position and/or orientation of the predefined section VD of the medical object MD in the vessel structure VS. In particular, vessel sections of the vessel structure running in a curved manner toward each other may result in a changed orientation of the predefined section VD of the medical object MD, in particular, with respect to the medical imaging device. The threshold value may describe a minimum change in the object parameter and/or the object path OP, with the processing unit 22 being configured for, in particular repeated, determination of the positioning of the medical imaging device relative to the examination object 31 when the threshold value is exceeded. The threshold value may also specify a minimum change in the orientation of the predefined section VD of the medical object MD in the vessel structure VS, therefore.

Figure 3:
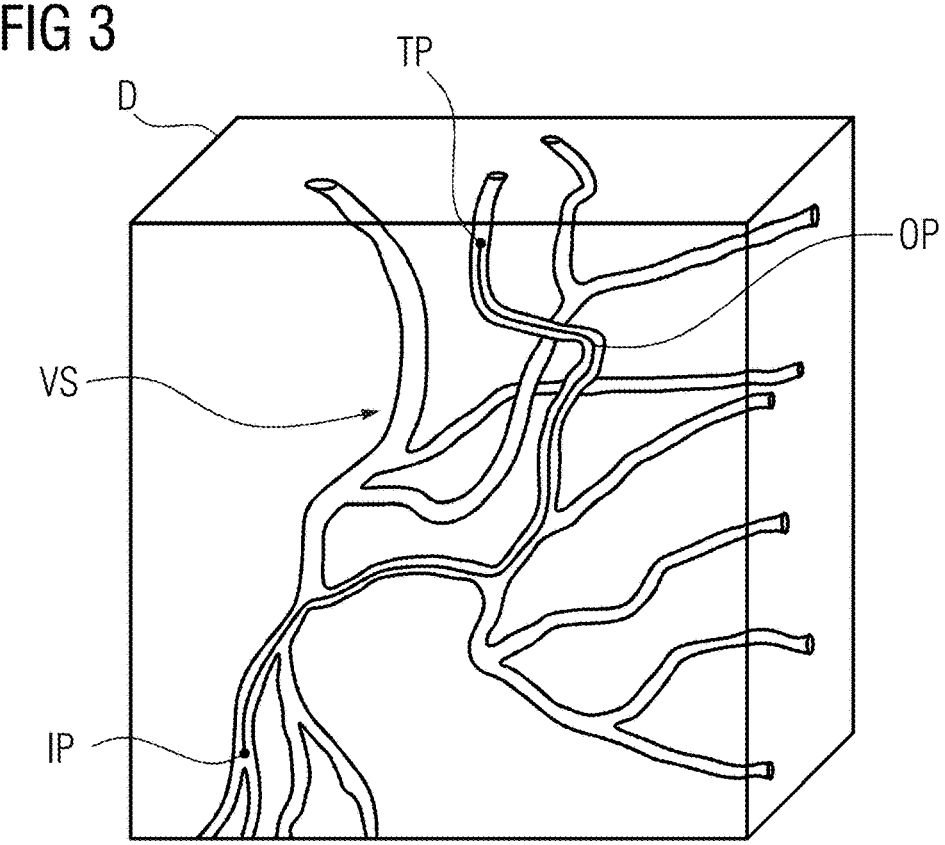
FIG. 3 depicts a schematic representation of an example of a data set with an object path.

FIG. 3 depicts a schematic representation of the data set D with object path OP. The data set D may include, (e.g., two-dimensionally and/or three-dimensionally), spatially resolved first image data from the examination object 31, (e.g., the vessel structure VS), which may be acquired preoperatively. In addition, the first image data may be, in particular additionally, temporally resolved. Furthermore, the data set D may have a model, in particular a three-dimensional one, (e.g., a volume network model and/or a central line model), of the vessel structure VS. The model may have been determined based on the first image data. The data set D may have a segmented mapping of the vessel structure VS of the examination object 31.

Furthermore, the data set D, in particular the mapping of the vessel structure VS, is registered with the medical imaging device. In other words, a coordinate system of the data set D may advantageously be registered with the coordinate system of the medical imaging device. A corresponding spatial position in the coordinate system of the medical imaging device may be assigned to each position in the data set D hereby. In addition, the data set D may advantageously be registered with a positioning of the examination object 31, in particular an instantaneous positioning.

Advantageously, a target region TP may be determined in the data set D. This may take place by a user input by the input element 41. The processing unit 22 may be configured to determine the object path OP along the vessel structure VS starting from an initial region IP toward the target region TP in the data set D. The initial region IP may mark the position of the entry of the medical object MD into the vessel structure VS, in particular on the introducer sheath. Advantageously, the object path OP may be determined three-dimensionally. Advantageously, a spatial position of the predefined section VD of the medical object MD in the coordinate system of the medical imaging device may be determined based on the object parameter and the data set.

The processing unit 22 may also be configured to adjust the object path OP based on the object parameter OP upon a deformation of the vessel structure VS due to the medical object MD arranged therein.

Figure 4:
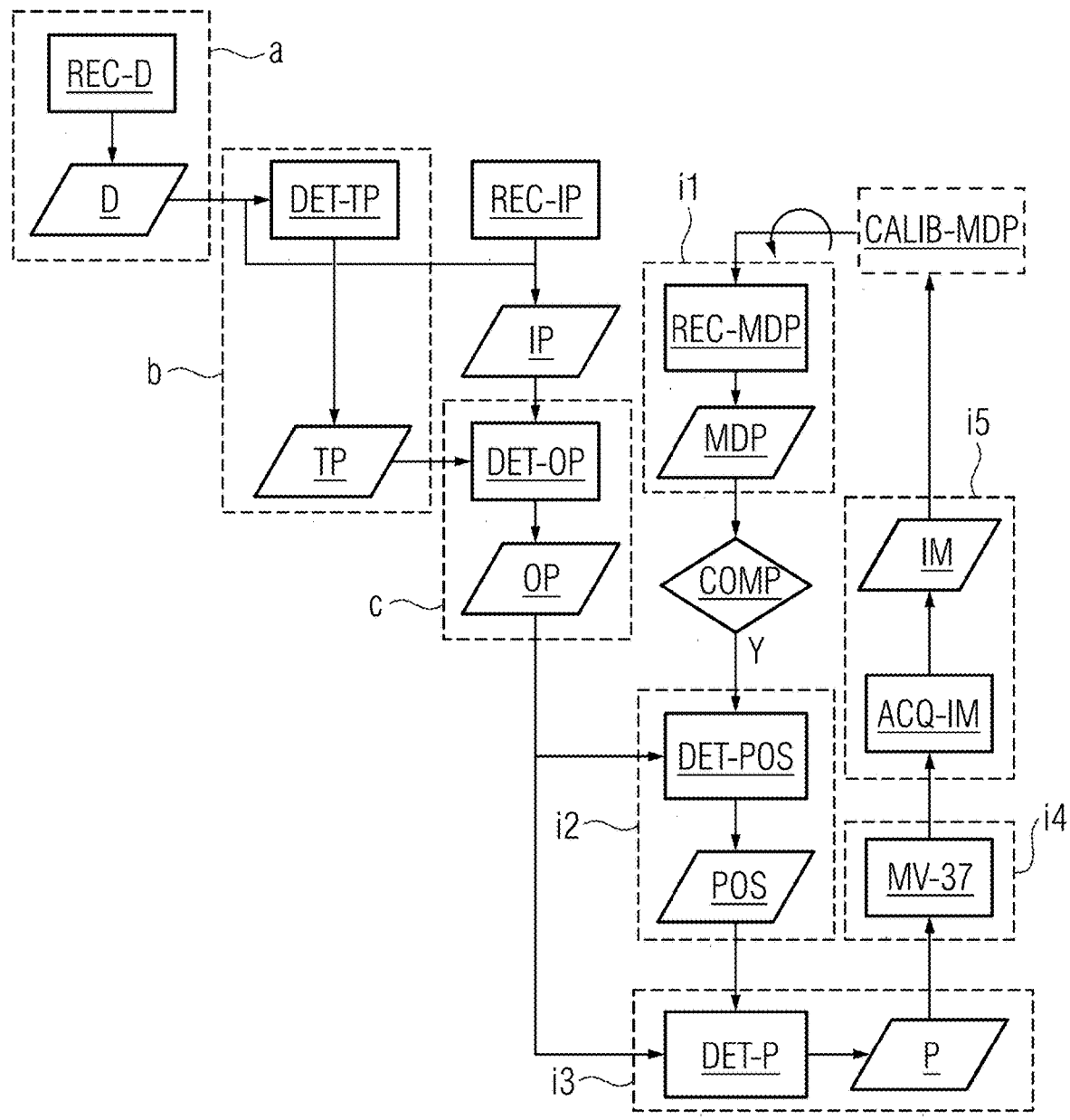
FIG. 4 depicts a schematic representation of an embodiment of the proposed method for control of a medical imaging device.

FIG. 4 depicts a schematic representation of an embodiment of the proposed method for control of a medical imaging device. The data set D may be received REC-D in act a). Hereafter in act b), the target region TP may be determined DET-TP in the data set D. In act c), the object path OP along the vessel structure VS toward the target region TP may be determined DET-OP in the data set D. In act i1), the object parameter MDP relating to the movement state of the medical object MD, which is arranged along the object path OP, may be received REC-MDP. Furthermore, a spatial position POS of the predefined section VS of the medical object MD may be determined DET-POS based on the object parameter MDP and the object path OP in act i2). In act i3), the positioning P of the medical X-ray apparatus relative to the examination object 31 may be determined DET-P based on the spatial position POS and the object path OP in such a way that the predefined section VD of the medical object MD may be mapped by the medical imaging device. In act i4), the medical imaging device may be moved MV-37 into the determined positioning P. Furthermore, the image data IM may be acquired ACQ-IM from the examination object 31 by the medical imaging device in act i5).

Advantageously, acts i1) to i5) may be repeatedly performed upon a change in the object parameter MDP and/or the object path OP.

If the object parameter MDP includes information relating to a movement distance of the medical object MD in respect of a spatial reference point, in particular the initial region IP, the object parameter MDP may be calibrated CALIB-MDP based on the image data IM and the determined positioning P of the medical imaging device when a distance threshold value is exceeded. Exceeding of the distance threshold value may be detected, in particular, by way of a comparison COMP.

The schematic representations contained in the described figures do not depict any kind of scale or proportions.

In conclusion, reference is made once again to the fact that the methods described in detail above and the illustrated devices are merely exemplary embodiments, which may be modified in a wide variety of ways by a person skilled in the art without departing from the scope of the disclosure. Furthermore, use of the indefinite article "a" or "an" does not preclude the relevant features from also being present several times. Similarly, the terms "unit" and "element" do not preclude the relevant components from including a plurality of cooperating sub-components, which may optionally also be spatially distributed.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A system for imaging a robotically moved medical object, the system comprising:
   a movement device for robotic movement of the medical object;
   a medical imaging device configured to acquire image data; and
   a processing unit configured to receive a data set, wherein the data set at least partially maps a vessel structure of an examination object and is registered with the medical imaging device,
   wherein the processing unit is further configured to determine an object path along the vessel structure toward a target region in the data set,
   wherein the movement device is configured to move the medical object along the object path, and provide an object parameter relating to a movement state of the medical object, and
   wherein the processing unit is further configured to control a positioning of the medical imaging device relative to the examination object as a function of the object parameter and the object path such that a predefined section of the medical object is mapped in the image data acquired by the medical imaging device.

2. The system of claim 1, wherein the medical imaging device is a medical X-ray apparatus,
   wherein the processing unit is further configured to control the positioning of the medical X-ray apparatus relative to the examination object such that an X-ray dose is optimized for acquisition of the image data.

3. The system of claim 1, wherein the processing unit is further configured to receive at least one positioning suggestion based on the object parameter and the object path, and
   wherein the processing unit is further configured to determine the positioning of the medical imaging device based on the at least one positioning suggestion.

4. The system of claim 1, wherein the movement device is configured to provide the object parameter comprising information relating to at least one of a speed, orientation, relative position, or movement distance of the medical object.

5. The system of claim 4, wherein the processing unit is further configured to repeatedly determine the positioning of the medical imaging device upon a change in the object parameter and/or the object path.

6. The system of claim 5, wherein the processing unit is further configured to repeatedly determine the positioning of the medical imaging device as a function of a threshold value in respect of the change in the object parameter and/or the object path.

7. The system of claim 6, wherein the processing unit is further configured to adjust the object path based on the object parameter upon a deformation of the vessel structure due to the medical object arranged therein.

8. The system of claim 1, wherein the processing unit is further configured to repeatedly determine the positioning of the medical imaging device upon a change in the object parameter and/or the object path.

9. The system of claim 8, wherein the processing unit is further configured to repeatedly determine the positioning of the medical imaging device as a function of a threshold value in respect of the change in the object parameter and/or the object path.

10. The system of claim 8, wherein the processing unit is further configured to adjust the object path based on the object parameter upon a deformation of the vessel structure due to the medical object arranged therein.

11. The system of claim 1, further comprising:
a patient supporting device configured to support the examination object,
wherein the processing unit is configured to control a movement of the patient supporting device and/or the medical imaging device such that the medical imaging device is positioned relative to the examination object, and the predefined section of the medical object is mapped in the image data acquired by the medical imaging device.

12. The system of claim 11, wherein the processing unit is further configured to adjust the object path based on the object parameter upon a deformation of the vessel structure due to the medical object arranged therein.

13. A method for control of a medical imaging device, the method comprising:
receiving a data set, wherein the data set at least partially maps a vessel structure of an examination object, and wherein the data set is registered with the medical imaging device;
determining, by a processing unit, a target region in the data set;
determining an object path along the vessel structure toward the target region in the data set;
receiving an object parameter relating to a movement state of a medical object, wherein the medical object is arranged along the object path;
determining a spatial position of a predefined section of the medical object based on the object parameter and the object path;
determining a positioning of the medical imaging device relative to the examination object based on of the spatial position and the object path such that the predefined section of the medical object is configured to be mapped by the medical imaging device;
moving the medical imaging device into the determined positioning; and
acquiring image data from the examination object by the medical imaging device.

14. The method of claim 13, wherein the object parameter comprises information relating to a movement distance of the medical object in respect of a spatial reference point, and wherein the object parameter is calibrated based on the image data and the determined positioning of the medical imaging device when a distance threshold value is exceeded.

15. The method of claim 13, wherein the receiving of the object parameter, the determining of the spatial position, the determining of the positioning of the medical imaging device, and the moving of the medical imaging device are repeatedly performed upon a change in the object parameter and/or the object path.

16. The method of claim 15, wherein the object parameter comprises information relating to a movement distance of the medical object in respect of a spatial reference point, and
wherein the object parameter is calibrated based on the image data and the determined positioning of the medical imaging device when a distance threshold value is exceeded.

17. A medical imaging device comprising:
a processing unit configured to:
receive a data set, wherein the data set at least partially maps a vessel structure of an examination object, and wherein the data set is registered with the medical imaging device;
determine a target region in the data set;
determine an object path along the vessel structure toward the target region in the data set;
receive an object parameter relating to a movement state of a medical object, wherein the medical object is arranged along the object path;
determine a spatial position of a predefined section of the medical object based on the object parameter and the object path; and
determine a positioning of the medical imaging device relative to the examination object based on of the spatial position and the object path such that the predefined section of the medical object is configured to be mapped by the medical imaging device,
wherein the medical imaging device is configured to be moved into the determined position and acquire image data from the examination object.

\* \* \* \* \*